United States Patent
Levy et al.

(10) Patent No.: US 9,895,323 B2
(45) Date of Patent: *Feb. 20, 2018

(54) ASTAXANTHIN ANTI-INFLAMMATORY SYNERGISTIC COMBINATIONS

(71) Applicant: Lycored Ltd., Beer Sheva (IL)

(72) Inventors: Rachel Levy, Omer (IL); Nurit Hadad, Beer Sheva (IL); Tanya Sedlov, Beer Sheva (IL); Morris Zelkha, Ramat Gan (IL)

(73) Assignee: LYCORED LTD., Beer Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/266,215

(22) Filed: Sep. 15, 2016

(65) Prior Publication Data

US 2017/0027884 A1    Feb. 2, 2017

Related U.S. Application Data

(63) Continuation of application No. 14/778,800, filed as application No. PCT/IL2014/050272 on Mar. 13, 2014, now Pat. No. 9,468,609.

(60) Provisional application No. 61/803,191, filed on Mar. 19, 2013.

(51) Int. Cl.
| | |
|---|---|
| *A61K 31/122* | (2006.01) |
| *A61K 31/01* | (2006.01) |
| *A61K 31/192* | (2006.01) |
| *A61K 9/00* | (2006.01) |
| *A61K 31/015* | (2006.01) |
| *A61K 31/047* | (2006.01) |
| *A61K 31/355* | (2006.01) |
| *A61K 36/81* | (2006.01) |
| *A23L 33/105* | (2016.01) |

(52) U.S. Cl.
CPC .......... *A61K 31/122* (2013.01); *A23L 33/105* (2016.08); *A61K 9/0053* (2013.01); *A61K 31/01* (2013.01); *A61K 31/015* (2013.01); *A61K 31/047* (2013.01); *A61K 31/192* (2013.01); *A61K 31/355* (2013.01); *A61K 36/81* (2013.01); *A23V 2002/00* (2013.01); *A61K 2300/00* (2013.01)

(58) Field of Classification Search
CPC .................................................... A61K 31/122
USPC ........................................................ 514/458
See application file for complete search history.

(56) References Cited

FOREIGN PATENT DOCUMENTS

| | | |
|---|---|---|
| CN | 101808626 A | 8/2010 |
| JP | 2010208972 A | 9/2010 |
| WO | 2004052351 | 6/2004 |
| WO | 2009007975 | 1/2009 |
| WO | 2007037438 A1 | 4/2009 |
| WO | 2010082205 A1 | 7/2010 |

OTHER PUBLICATIONS

Lee et al., "Astaxanthin inhibits nitric oxide production and inflammatory gene expression by suppressing IKB kinase-dependent NF-KB activation", Molecules and Cells {Impact Factor: 2.09). Sep. 2003; 16(1):97-105.
Palozza et al., "Tomato lycopene and inflammatory cascade: basic interactions and clinical implications". Curr Med Chem. 2010;17(23):2547-63.
Hadad et al., "The synergistic anti-inflammatory effects of lycopene, lutein, β-carotene, and carnosic acid combinations via redox-based inhibition of NF-KB signaling". Free Radical Biology and Medicine vol. 53, Issue 7, Oct. 1, 2012, pp. 1381-1391.
Rafi et al., "Dietary lutein modulates inducible nitric oxide synthase (iNOS) gene and protein expression in mouse macrophage cells (RAW 264.7)" Molecular Nutrition & Food Research, vol. 51, Issue 3, pp. 333-340, Mar. 2007.
Rafi et al., "Lycopene inhibits LPS induced pro-inflammatory mediators in mouse macrophage cells." Journal of Food Science, 72: 69-74 (2007).
Choi et al., "Inhibition of nNOS and COX-2 expression by lutein in acute retinal ischemia." Nutrition. Jun. 2006;22(6):668-71. Epub May 2, 2006.
Anonymous, "Higher Nature Astaxanthine and Balckcurrant Capsules Pack of 90: Amazon.co.uk: Health & Personal Care", Retrieved from the Internet—URL: http://www.amazon.co.uk/dp/B000NRVW2U?_encoding=UTF8&islnlframe=0&n=65801031 &ref_=dp_[rpddesc_0&s=drugsore &showDetailProductDesc=1#product-description_feature_div Published Feb. 26, 2007, pp. 1-6, as retrieved on Sep. 22, 2016.
Greenspan, D., "Salmon with Tomatoes & Rosemary", Retrieved from the Internet—URL: http://communitytable.parade.com/30359/doriegreenspan/salmon-with-tomatoes-rosemary/ Published 263 Jul. 2011, pp. 1-3, as retrieved on Sep. 22, 2016.

*Primary Examiner* — Taofiq A Solola
(74) *Attorney, Agent, or Firm* — The Roy Gross Law Firm, LLC; Roy Gross

(57) ABSTRACT

Compositions having synergistic combinations of astaxanthin with a tomato extract lycopene, and optionally with carnosic acid and/or lutein. Compositions having synergistic combinations of the aforementioned compounds, which may be used, inter alia, to inhibit/suppress inflammation via the suppression of the expression of anti-inflammatory mediators or via the suppression of the secretion of anti-inflammatory mediators from macrophages at a site of inflammation.

10 Claims, 7 Drawing Sheets

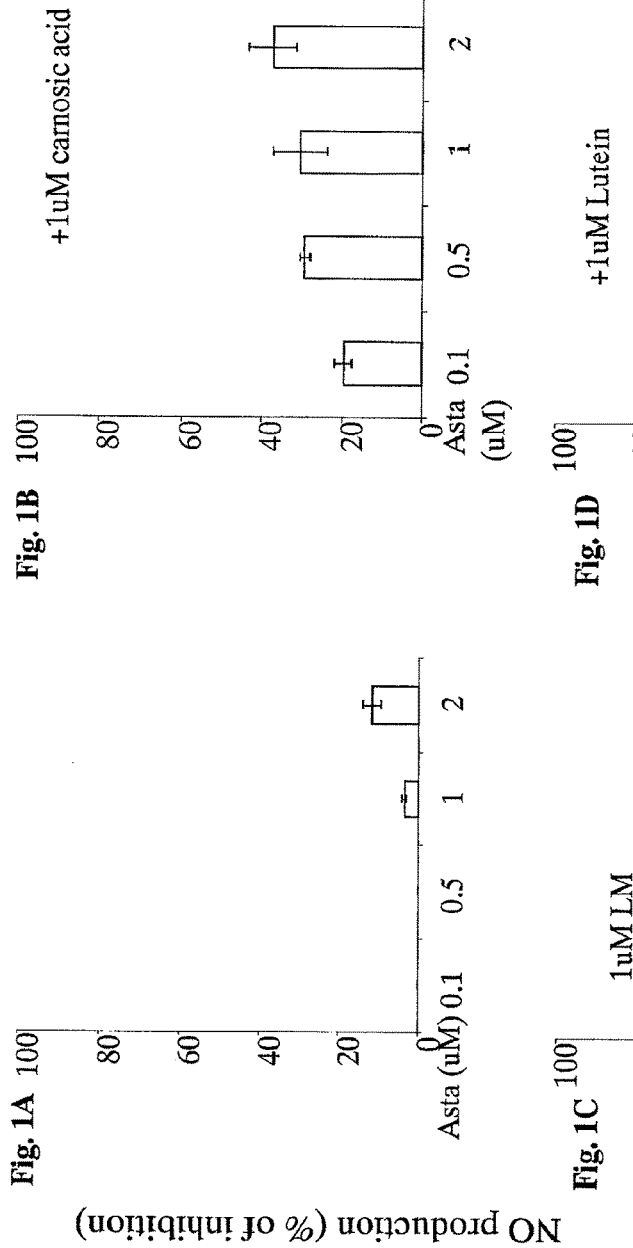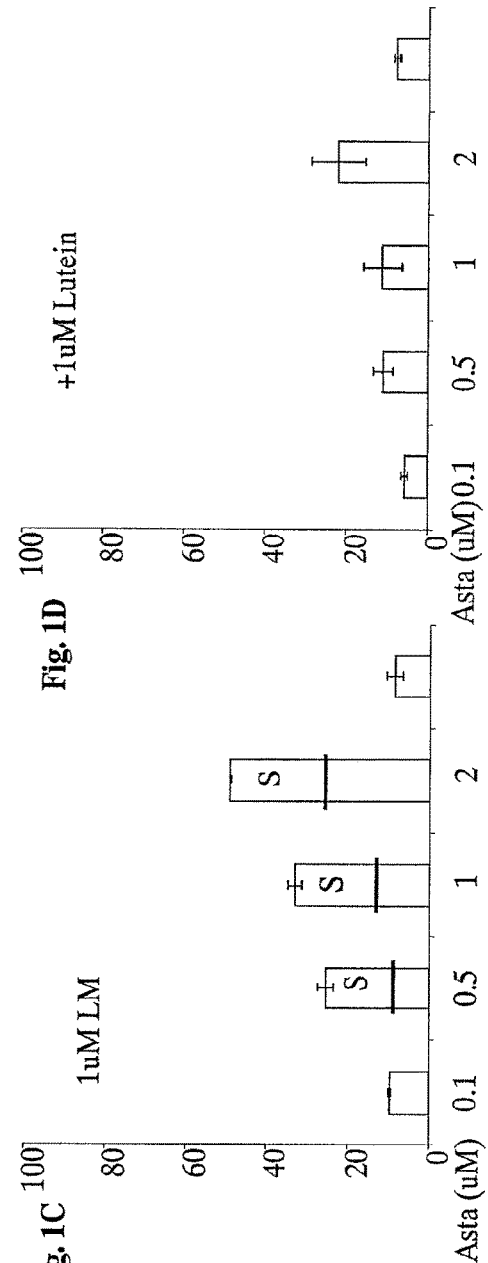

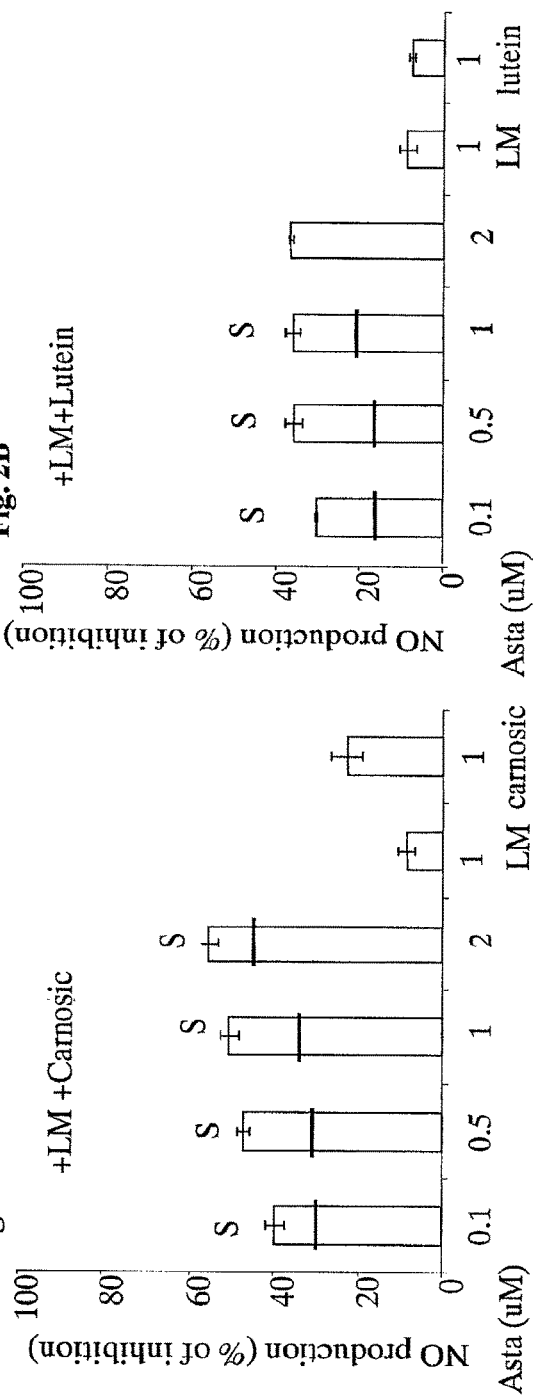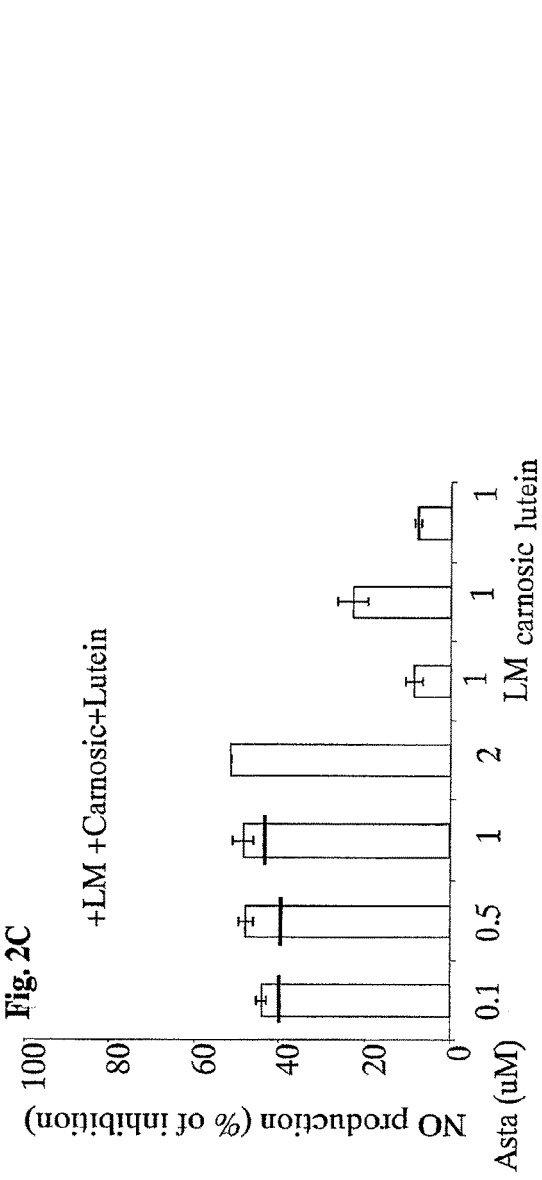

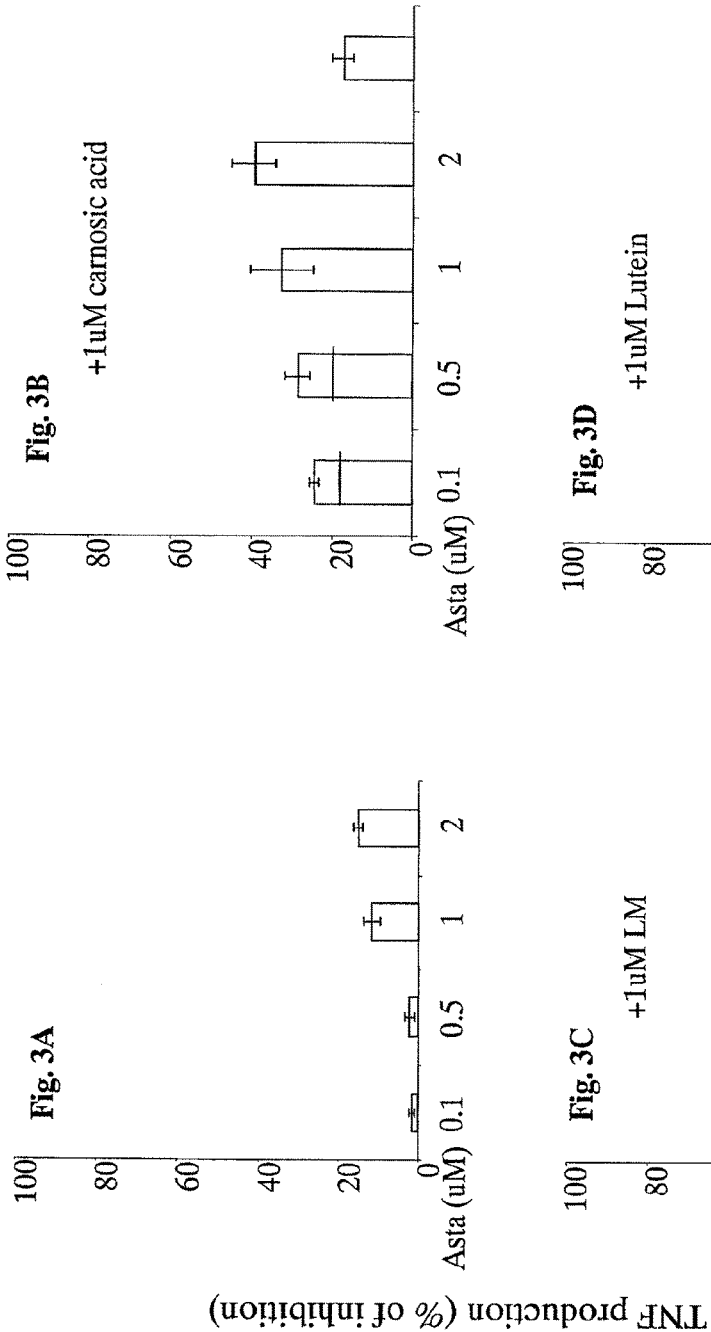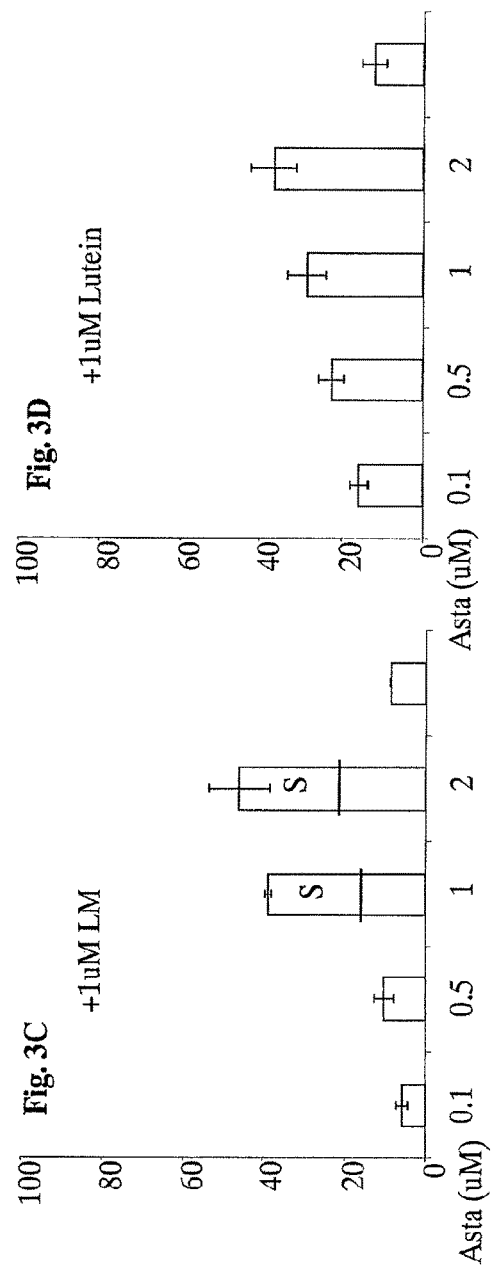

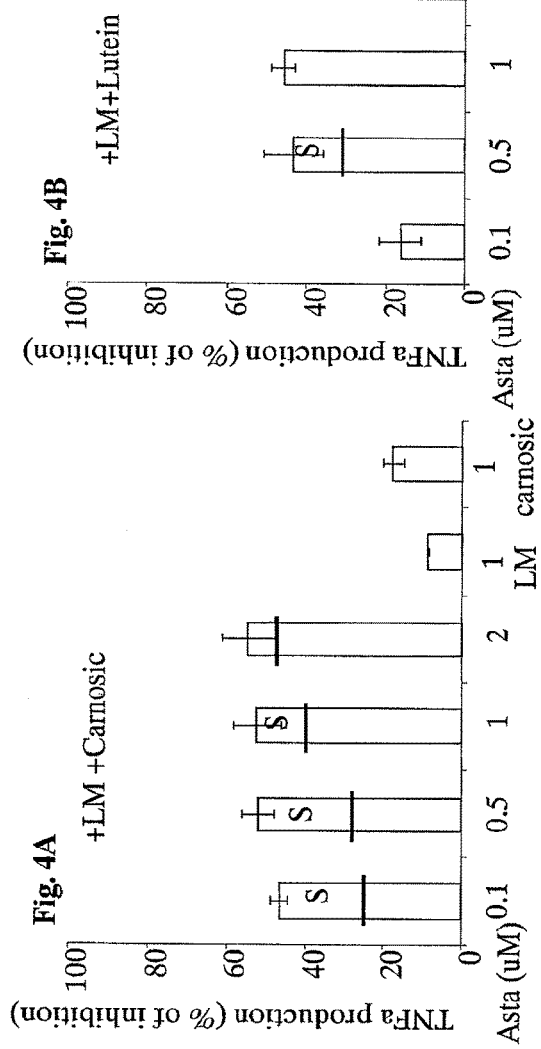
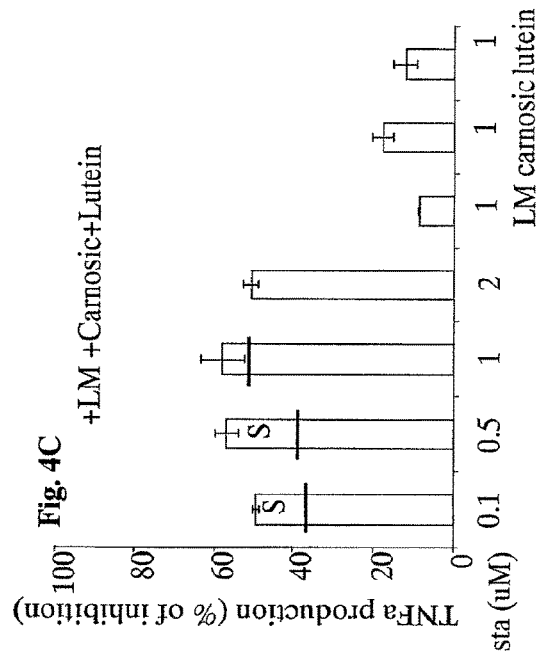
Fig. 4A, Fig. 4B, Fig. 4C

ASTAXANTHIN ANTI-INFLAMMATORY SYNERGISTIC COMBINATIONS

RELATED APPLICATIONS

This application is a continuation of U.S. Ser. No. 14/778,800 filed Sep. 21, 2015, which is a U.S. national phase of International Application No. PCT/IL2014/050272 filed Mar. 13, 2014, which claims the benefit of the filing date of U.S. Provisional Patent Application Ser. No. 61/803,191, filed Mar. 19, 2013. The contents of the above applications are all incorporated by reference as if fully set forth herein in their entirety.

FIELD OF INVENTION

This invention is directed to; inter alia, compositions comprising synergistic combinations of astaxanthin with lycopene, and optionally with carnosic acid and/or lutein. More specifically, the present invention provides a composition comprising a synergistic combination of the aforementioned compounds, which may be used, inter alia, to inhibit/suppress inflammation.

BACKGROUND OF THE INVENTION

The inflammatory process, which forms an important part of the non-specific immune system, is characterized by a complex set of chemical and cellular changes that are essential for host defense in the face of microbial agents and other potentially harmful environmental factors. However, in many cases, inflammation may be triggered inappropriately, and/or may persist to a degree which becomes harmful to the host. In such cases, there may be a need to inhibit or prevent the development of one or more aspects of the inflammatory process, in particular, in cases of non-infectious inflammatory diseases.

A very large number of different chemical mediators have been shown to be involved in the development and control of the inflammatory process. Recent studies by a number of different laboratories have implicated nitric oxide (NO) as an important modulator of a variety of acute and chronic inflammatory disorders, including various types of arthritis, gastro-intestinal diseases, inflammatory conditions of the central nervous system and certain forms of asthma. Consequently, it has been proposed that inhibition of NO production could provide a useful therapeutic mechanism for the treatment and/or management of these inflammatory disorders. Furthermore, inhibition of NO synthesis has also been shown to be useful in some conditions or states that are not primarily inflammatory in nature. Thus, for example, inhibition of NO synthesis has been found to reduce glucose uptake into limb tissue in individuals with Type 2 diabetes during exercise.

The in vivo production of NO is mediated by a family of nitric oxide synthase (NOS) enzymes, including inducible-nitric oxide synthase (I-NOS), which is activated by many different immunological stimuli including lipopolysaccharide (LPS), interferon gamma and interleukin 1 (IL-1).

Several other compounds, including a number of natural products, have also been shown to inhibit NO production. The latter group includes compounds such as lutein [Rafi M. M. et al. Mol Nutr Food Res. 2007 March; 51(3):333-40; Choi, J. S. Nutrition. 2006 June; 22(6):668-71] and lycopene [Rafi, M. M. et al. J Food Sci. 2007 January; 72(1):S069-74]. However, the efficacy and potency of many of the natural product NO inhibitors have proven to be not particularly high. A need therefore exists for improved NO production-inhibiting compositions of natural origin.

Another highly important inflammatory mediator is the tumor necrosis factor-alpha (TNF-alpha), which is a cytokine produced by a variety of cell types including macrophages, neutrophils and lymphocytes. TNF-alpha occupies a key position in the early stage of the inflammatory process and is responsible for stimulating the production of other factors such as nuclear factor-κB which in turn causes activation of a wide range of pro-inflammatory genes. Thus, in view of its key pro-inflammatory role, TNF-alpha is clearly an important potential therapeutic target for anti-inflammatory agents.

It is a purpose of the present invention to provide a composition that may be used to inhibit the production of one or more key inflammatory mediators, such as superoxide NO or TNF-alpha, as a means for treating or managing pathological states and processes in which said mediators are implicated.

It is another purpose of the invention to provide a composition that is able to inhibit the production of the aforesaid inflammatory mediators with greater efficacy and/or potency than the compounds and compositions reported in the prior art.

SUMMARY OF THE INVENTION

In one embodiment, the present invention provides a composition comprising tomato lycopene such as but not limited to Lyc-O-Mato® and astaxanthin.

In another embodiment, the present invention further provides a composition comprising astaxanthin, carnosic acid, and tomato lycopene.

In another embodiment, the present invention further provides a composition comprising astaxanthin, lutein, and tomato lycopene.

In another embodiment, the present invention further provides a composition comprising astaxanthin, carnosic acid, lutein, and tomato lycopene.

In another embodiment, the present invention further provides that the composition further comprises lutein, phytoene, phytofluene, beta-carotene, tocopherols, phytosterols, or any combination thereof. In another embodiment, the present invention further provides that the molar concentration ratio of astaxanthin to tomato lycopene is from 6:1 to 1:2. In another embodiment, the present invention further provides that the molar concentration ratio of astaxanthin to carnosic acid is from 1:1 to 1:10. In another embodiment, the present invention further provides that the molar concentration ratio of astaxanthin to tomato lycopene to carnosic acid is from 1:2:1 to 1:5:10. In another embodiment, the present invention further provides that the composition has a synergistic anti-inflammatory effect.

In another embodiment, the present invention further provides a method for treating a subject afflicted with inflammation, comprising the step of administering to the subject a therapeutically effective amount of a composition comprising: (1) astaxanthin, (2) lutein and/or carnosic acid, and (3) tomato lycopene, thereby treating a subject afflicted with inflammation. In another embodiment, the present invention further provides that treating a subject afflicted with inflammation is inhibiting the production of NO, PGE2, TNF-alpha, or any combination thereof.

BRIEF DESCRIPTION OF THE DRAWINGS

FIGS. 1A-1D are bar graphs showing the effect of various compositions of the invention including combinations of active ingredients on the NO production by LPS-stimulated macrophages. FIG. 1A provides a composition which includes astaxanthin (AST); FIG. 1B provides a composition which includes AST and carnosic acid (CA); FIG. 1C provides a composition which includes tomato lycopene extract and AST; and FIG. 1D provides a composition which includes lutein and AST. The effect of these compositions on the production of NO in LPS induced macrophages was tested. The Y axis provides a measure of inhibition of NO production by LPS-stimulated macrophages.

FIGS. 2A-2C Are bar graphs showing the effect of various compositions of the invention (including combinations of active ingredients) on the NO production by LPS-stimulated macrophages: FIG. 2A is AST, tomato lycopene extract, and carnosic acid (CA); AST, FIG. 2B is tomato lycopene extract, and lutein; and FIG. 2C is AST, tomato lycopene extract, lutein, and carnosic acid on the production of NO in LPS induced macrophages.

FIGS. 3A-3D are bar graphs showing the effect of various compositions of the invention (including combinations of active ingredients) on the TNF-alpha production by LPS-stimulated macrophages: FIG. 3A is astaxanthin (AST); FIG. 3B is AST and carnosic acid (CA); FIG. 3C is tomato lycopene extract and AST; and FIG. 3D is lutein and AST on the production of TNF-alpha in LPS induced macrophages.

FIGS. 4A-4C are bar graphs showing the effect of various compositions of the invention (including combinations of active ingredients) on the TNF-alpha production by LPS-stimulated macrophages: FIG. 4A is AST, tomato lycopene extract, and carnosic acid (CA); FIG. 4B is AST, tomato lycopene extract, and lutein; and FIG. 4C is AST, tomato lycopene extract, lutein, and carnosic acid on the production of TNF-alpha in LPS induced macrophages.

DETAILED DESCRIPTION OF THE INVENTION

Figure 5:
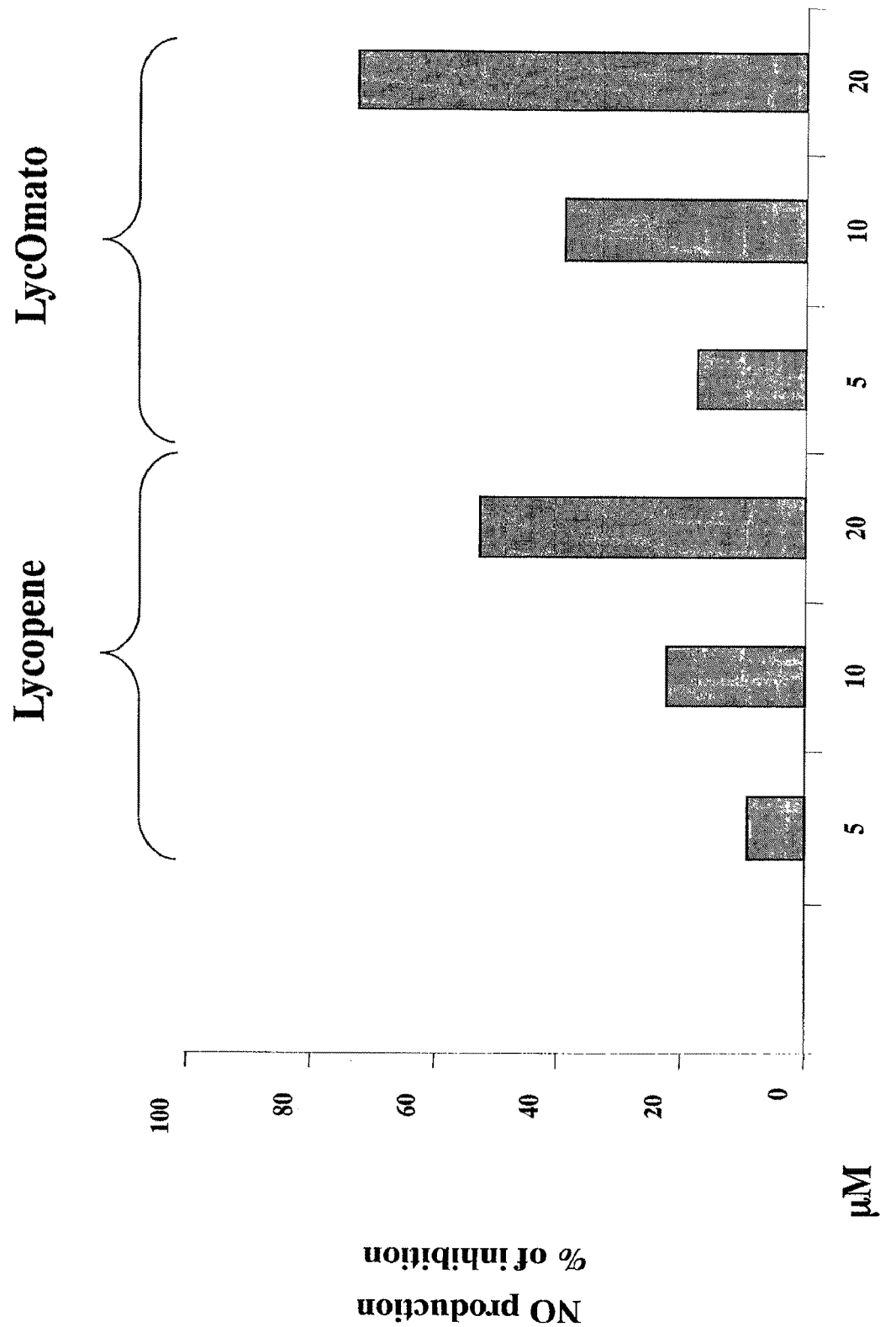
FIG. 5 is a bar graph showing the anti-inflammatory effect (NO production of LPS induced macrophages) of synthetic lycopene versus tomato extract lycopene.

In one embodiment, the present invention provides a composition comprising astaxanthin and tomato lycopene. In one embodiment, the present invention provides a composition comprising astaxanthin, carnosic acid, and tomato lycopene. In one embodiment, the present invention provides a composition comprising astaxanthin, lutein, and tomato lycopene. In one embodiment, the present invention provides a composition comprising astaxanthin, lutein, carnosic acid, and tomato lycopene.

In another embodiment, tomato lycopene is lycopene extracted from a tomato plant. In another embodiment, tomato lycopene is a tomato extract enriched for lycopene. In another embodiment, tomato lycopene is a lycopene-rich tomato extract which is all-natural. In another embodiment, tomato lycopene is a tomato lycopene complex. In another embodiment, tomato lycopene complex comprises a complex of phytonutrients including phytoene, phytofluene, beta-carotene, tocopherols and phytosterols. In another embodiment, tomato lycopene is Lyc-O-Mato® (LycoRed Ltd., Be'er Sheva, Israel). In another embodiment, a composition of the invention comprises Lyc-O-Mato® and astaxanthin.

Suitable processes for preparing this extract and similar extracts are described in U.S. Pat. No. 5,837,311, the specification of which is incorporated herein by reference in its entirety. However, it is to be recognized that many other types of preparatory procedures may be used to obtain the composition from a variety of plant sources.

In another embodiment, asthaxanthin is an ester of mainly di-palmitate. In another embodiment, astaxanthin is extracted and/or purified from microalgae. In another embodiment, astaxanthin is extracted and/or purified from yeast. In another embodiment, astaxanthin is extracted and/or purified from salmon. In another embodiment, astaxanthin is extracted and/or purified from trout. In another embodiment, astaxanthin is extracted and/or purified from krill. In another embodiment, astaxanthin is extracted and/or purified from shrimp. In another embodiment, astaxanthin is extracted and/or purified from crayfish. In another embodiment, astaxanthin is extracted and/or purified from a crustacean. In another embodiment, astaxanthin is extracted and/or purified from a feathers bird. In another embodiment, astaxanthin is synthetic astaxanthin. In another embodiment, synthetic astaxanthin is produced by a synthesis path such as but not limited to the synthesis path described in Krause, Wolfgang; Henrich, Klaus; Paust, Joachim; et al. Preparation of Astaxanthin. DE 19509955.9 Mar. 18, 1995.

In another embodiment, astaxanthin is produced in bacteria via an engineered production system. In another embodiment, astaxanthin biosynthesis proceeds from beta-carotene via either zeaxanthin or canthaxanthin. In another embodiment, astaxanthin is the 3R,3'R stereoisomer, the 3R,3'S (meso) stereoisomer, the 3S,3'S stereoisomer, or any combination thereof. In another embodiment, astaxanthin contains a mixture of the three stereoisomers in approximately 1:2:1 proportion.

In another embodiment, astaxanthin, which is a naturally-occurring compound and is a potent antioxidant, is used in a composition of the invention for ameliorating and retarding, and/or preventing, inflammatory or inflammatory induced traumatic disease or injury. In another embodiment, the composition as described herein has a synergistic ability to act as an anti-inflammatory, antioxidant.

In another embodiment, a composition as described herein further comprises phytoene. In another embodiment, a composition as described herein further comprises phytofluene. In another embodiment, a composition as described herein further comprises beta-carotene. In another embodiment, a composition as described herein further comprises tocopherol. In another embodiment, a composition as described herein further comprises a phytosterol. In another embodiment, a composition as described herein further comprises a combination of any two or more of: phytoene, phytofluene, beta-carotene, tocopherol, and phytosterol. In another embodiment, phytoene, phytofluene, beta-carotene, tocopherol, and phytosterol are of natural source. In another embodiment, phytoene, phytofluene, beta-carotene, tocopherol, and phytosterol are derived from tomato. In another embodiment, phytoene, phytofluene, beta-carotene, tocopherol, phytosterol, or any combination thereof is produced synthetically. In another embodiment, phytosterol can be a combination of phytosterols.

In another embodiment, the molar concentration ratio of astaxanthin to tomato lycopene is from 20:1 to 1:5. In another embodiment, the molar concentration ratio of astaxanthin to tomato lycopene is from 15:1 to 1:2. In another embodiment, the molar concentration ratio of astaxanthin to tomato lycopene is from 10:1 to 1:5. In another embodiment, the molar concentration ratio of astaxanthin to tomato lycopene is from 6:1 to 1:5. In another embodiment, the molar concentration ratio of astaxanthin to tomato lycopene is from 6:1 to 1:2.

In another embodiment, a composition as described comprises from 2.5 to 15 mg tomato lycopene. In another embodiment, a composition as described comprises 5 mg tomato lycopene. In another embodiment, a composition as described comprises from 5 to 10 mg tomato lycopene. In another embodiment, a composition as described comprises 0.5 to 100 mg astaxanthin. In another embodiment, a composition as described comprises 10 to 100 mg astaxanthin. In another embodiment, a composition as described comprises 10 to 50 mg astaxanthin. In another embodiment, a composition as described comprises 20 to 50 mg astaxanthin. In another embodiment, a composition as described comprises 10 mg to 10 g carnosic acid. In another embodiment, a composition as described comprises 10 mg to 1 g carnosic acid. In another embodiment, a composition as described comprises 10 to 500 mg carnosic acid. In another embodiment, a composition as described comprises 50 to 500 mg carnosic acid. In another embodiment, a composition as described comprises 100 to 500 mg carnosic acid.

In another embodiment, the molar concentration ratio of astaxanthin to carnosic acid in a composition of the invention is from 1:1 to 1:50. In another embodiment, the molar concentration ratio of astaxanthin to carnosic acid in a composition of the invention is from 1:1 to 1:20. In another embodiment, the molar concentration ratio of astaxanthin to carnosic acid in a composition of the invention is from 1:1 to 1:10. In another embodiment, the molar concentration ratio of astaxanthin to carnosic acid in a composition of the invention is from 1:1 to 1:5.

In another embodiment, the molar concentration ratio of astaxanthin to tomato lycopene to carnosic acid in a composition of the invention is from 1:1:1 to 1:20:40. In another embodiment, the molar concentration ratio of astaxanthin to tomato lycopene to carnosic acid in a composition of the invention is from 1:1:1 to 1:10:20. In another embodiment, the molar concentration ratio of astaxanthin to tomato lycopene to carnosic acid in a composition of the invention is from 1:1:1 to 1:10:10. In another embodiment, the molar concentration ratio of astaxanthin to tomato lycopene to carnosic acid in a composition of the invention is from 1:2:1 to 1:5:10.

In another embodiment, a composition of the invention further comprises zeaxanthin. In another embodiment, a composition of the invention further comprises lutein. In another embodiment, lutein comprises (3R,3'R,6'R)-beta, epsilon-carotene-3,3'-diol. In another embodiment, lutein is a plant lutein. In another embodiment, lutein is tomato lutein. In another embodiment, lutein is marigold lutein. In another embodiment, lutein is provided as a marigold extract. In another embodiment, lutein is a synthetic lutein. In another embodiment, lutein comprises saponifying fatty acid.

The components of the above-disclosed compositions may be purified compounds, synthetic compounds or may be present in mixture with other components, for example in plant extracts such as rosemary extract (in the case of carnosic acid), marigold extract (in the case of lutein) or a tomato extract (such as Lyc-O-Mato® which is commercially available from LycoRed, Be'er Sheva, Israel—in the case of lycopene and other carotenoids). In some embodiments, carnosic acid is supplied as rosemary extract. In some embodiments, carnosic acid is obtained from a rosemary extract.

In some embodiments, a composition as described herein has a synergistic anti-inflammatory effect. In some embodiments, a composition as described herein is an oral composition. In some embodiments, a composition as described herein further comprises a pharmaceutical or a nutraceutical acceptable excipient.

In some embodiments, a composition as described herein inhibits the production and/or secretion of inflammatory mediators and cytokines which play important roles in the pathogenesis of a vast number of mammalian inflammatory diseases. In another embodiment, a composition of the invention is a phytonutrient combination causing an immediate, efficient, and synergistic inhibition of LPS-induced internal superoxide production leading to a marked decrease in ERK and NF-kB activation.

In another embodiment, the present invention further provides a method for treating a subject afflicted with inflammation or septic shock, comprising the step of administering to the subject a therapeutically effective amount of a composition as described herein. In another embodiment, the present invention further provides a method for inhibiting the production of proinflammatory cytokines, such as but not limited to TNF-alpha by macrophages and monocytes at inflammatory sites comprising the step of administering to a subject in need thereof, a therapeutically effective amount of a composition as described herein. In another embodiment, the present invention further provides a method for inhibiting the release of proinflammatory cytokines, such as but not limited to TNF-alpha by macrophages and monocytes at inflammatory sites comprising the step of administering to a subject in need thereof, a therapeutically effective amount of a composition as described herein.

In another embodiment, the present invention further provides a method for treating a subject afflicted with inflammation, wherein the inflammation is an inherent part of a disease state. In another embodiment, the present invention further provides a method for treating rheumatoid arthritis. In another embodiment, the present invention further provides a method for treating Crohn's disease. In another embodiment, the present invention further provides a method for treating ulcerative colitis. In another embodiment, the present invention further provides a method for treating septic shock syndrome. In another embodiment, the present invention further provides a method for treating atherosclerosis. In another embodiment, the present invention further provides a method for treating juvenile rheumatoid arthritis. In another embodiment, the present invention further provides a method for treating psoriatic arthritis. In another embodiment, the present invention further provides a method for treating osteoarthritis. In another embodiment, the present invention further provides a method for treating refractory rheumatoid arthritis. In another embodiment, the present invention further provides a method for treating chronic non-rheumatoid arthritis. In another embodiment, the present invention further provides a method for treating osteoporosis/bone resorption. In another embodiment, the present invention further provides a method for treating endotoxic shock. In another embodiment, the present invention further provides a method for treating ischemia-reperfusion injury. In another embodiment, the present invention further provides a method for treating coronary heart disease. In another embodiment, the present invention further provides a method for treating vasculitis. In another embodiment, the present invention further provides a method for treating amyloidosis. In another embodiment, the present invention further provides a method for treating multiple sclerosis. In another embodiment, the present invention further provides a method for treating sepsis. In another embodiment, the present invention further provides a method for treating chronic recurrent uveitis. In another embodiment, the present invention further provides a method for treating hepatitis C virus infection. In another embodiment, the present invention further provides a method for treating malaria. In another embodiment, the present invention further provides a method for treating ulcerative colitis. In another embodiment, the present invention further provides a method for treating cachexia. In another embodiment, the present invention further provides a method for treating plasmocytoma. In another embodiment, the present invention further provides a method for treating endometriosis. In another embodiment, the present invention further provides a method for treating Behcet's disease. In another embodiment, the present invention further provides a method for treating Wegenrer's granulomatosis. In another embodiment, the present invention further provides a method for treating an autoimmune disease. In another embodiment, the present invention further provides a method for treating ankylosing spondylitis. In another embodiment, the present invention further provides a method for treating common variable immunodeficiency (CVID). In another embodiment, the present invention further provides a method for treating chronic graft-versus-host disease. In another embodiment, the present invention further provides a method for treating trauma and transplant rejection. In another embodiment, the present invention further provides a method for treating adult respiratory distress syndrome. In another embodiment, the present invention further provides a method for treating pulmonary fibrosis. In another embodiment, the present invention further provides a method for treating recurrent ovarian cancer. In another embodiment, the present invention further provides a method for treating a lymphoproliferative disease. In another embodiment, the present invention further provides a method for treating refractory multiple myeloma. In another embodiment, the present invention further provides a method for treating myeloproliferative disorder. In another embodiment, the present invention further provides a method for treating diabetes. In another embodiment, the present invention further provides a method for treating juvenile diabetes. In another embodiment, the present invention further provides a method for treating meningitis. In another embodiment, the present invention further provides a method for treating skin delayed type hypersensitivity disorders. In another embodiment, the present invention further provides a method for treating Alzheimer's disease. In another embodiment, the present invention further provides a method for treating systemic lupus erythematosus. In another embodiment, the present invention further provides a method for treating any other clinical condition which is inherently associated or depends on an inflammatory process.

In another embodiment, the present invention provides that treating a subject afflicted with inflammation is inhibiting the production of an anti-inflammatory cytokine, a glucocorticoid, an anti-inflammatory neuropeptide, or a lipid inflammation mediator. In another embodiment, the present invention provides that treating a subject afflicted with inflammation is inhibiting the production of NO, PGE, TNF-alpha, or any combination thereof at a site of inflammation. In another embodiment, the present invention provides that treating a subject afflicted with inflammation is inhibiting the production of NO, PGE, TNF-alpha, or any combination thereof by macrophages. In another embodiment, the present invention provides that treating a subject afflicted with inflammation is inhibiting the recruitment of neutrophils to the site of inflammation. In another embodiment, the present invention provides that treating a subject afflicted with inflammation is inhibiting neutrophils activation at the site of inflammation. In another embodiment, PGE is PGE2 (prostaglandin E2).

Furthermore, the present invention also provides a method of treatment of pathological conditions in which superoxide ions, NO, TNF-alpha and/or PGE2 act as a modulator or mediator of the condition in a mammalian subject in need of such treatment, wherein the method comprises administering to the subject a therapeutic composition according to any one of the embodiments disclosed hereinabove.

In another aspect, the present invention is directed to the use of a composition such as described herein for the manufacture of a medicament for the treatment of conditions responsive to inhibition of NO, TNF-alpha and/or PGE2 production.

In some embodiments of the methods described hereinabove, the subject is a human subject. In some embodiments of the methods described hereinabove, the subject is a mammal. In some embodiments of the methods described hereinabove, the subject is a pet. In some embodiments of the methods described hereinabove, the subject is a farm animal. In some embodiments of the methods described hereinabove, the subject is a lab animal.

While in the above-disclosed methods, the therapeutic composition may be administered by any convenient means, in one embodiment the composition is administered in a pharmaceutical, a nutraceutical, nutritional, or oral dosage form. In another preferred embodiment, however, the therapeutic composition is incorporated into a foodstuff or beverage.

In one embodiment, the composition of the present invention can be provided to the individual per-se. In one embodiment, the composition of the present invention can be provided to the individual as part of a further pharmaceutical composition or a nutraceutical composition where it is mixed with a pharmaceutically acceptable carrier.

In one embodiment, a "pharmaceutical composition" or a "nutraceutical composition" refers to a preparation of a composition as described herein with other chemical components such as physiologically suitable carriers and excipients. The purpose of a pharmaceutical composition or a nutraceutical composition is to facilitate administration of the composition to an organism.

In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrases "physiologically acceptable carrier" and "pharmaceutically acceptable carrier" which be interchangeably used refer to a carrier or a diluent that does not cause significant irritation to a mammal and does not abrogate the biological activity and properties of the administered composition. An adjuvant is included under these phrases.

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference in its entirety.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body. In one embodiment, the region of a patient's body is characterized by inflammation or as comprising inflammatory mediators.

Various embodiments of dosage ranges are contemplated by this invention. The dosage of the composition of the present invention, in one embodiment, is in the range of 0.5-2000 mg/day. In another embodiment, the dosage is in the range of 5-500 mg/day. In another embodiment, the dosage is in the range of 500-2000 mg/day. In another embodiment, the dosage is in the range of 0.1-10 mg/day. In another embodiment, the dosage is in the range of 50-500 mg/day. In another embodiment, the dosage is in the range of 5-4000 mg/day. In another embodiment, the dosage is in the range of 0.5-50 mg/day. In another embodiment, the dosage is in the range of 5-80 mg/day. In another embodiment, the dosage is in the range of 100-1000 mg/day. In another embodiment, the dosage is in the range of 1000-2000 mg/day. In another embodiment, the dosage is in the range of 200-600 mg/day. In another embodiment, the dosage is in the range of 400-1500 mg/day. In another embodiment, the dosage is in a range of 800-1500 mg/day. In another embodiment, the dosage is in the range of 500-2500 mg/day. In another embodiment, the dosage is in a range of 600-1200 mg/day. In another embodiment, the dosage is in the range of 1200-2400 mg/day. In another embodiment, the dosage is in the range of 40-60 mg/day. In another embodiment, the dosage is in a range of 2400-4000 mg/day. In another embodiment, the dosage is in a range of 450-1500 mg/day. In another embodiment, the dosage is in the range of 1500-2500 mg/day. In another embodiment, the dosage is in the range of 5-10 mg/day. In another embodiment, the dosage is in the range of 550-1500 mg/day. In another embodiment, "dosage" refers to the amount of an active ingredient or the combination of active ingredients of the invention. In another embodiment, "dosage" is not inclusive with respect to excipients. Aqueous solutions, buffers, vehicles, or any other inert substance.

In one embodiment, the dosage is 200 mg/day. In another embodiment, the dosage is 300 mg/day. In another embodiment, the dosage is 400 mg/day. In another embodiment, the dosage is 500 mg/day. In another embodiment, the dosage is 600 mg/day. In another embodiment, the dosage is 700 mg/day. In another embodiment, the dosage is 800 mg/day. In another embodiment, the dosage is 900 mg/day. In another embodiment, the dosage is 1000 mg/day.

Oral administration, in one embodiment, comprises a unit dosage form comprising tablets, capsules, lozenges, chewable tablets, suspensions, drinks, syrups, nectars, beverages, emulsions and the like. Such unit dosage forms comprise a safe and effective amount of the composition. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the active ingredient as known to one skilled in the art. In another embodiment, the composition is a drink or a beverage comprising a dosage which consists a combination of the active ingredients in a ratio or in an amount as described herein.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.012% to about 0.933% of the active ingredients, or in another embodiment, from about 0.033% to about 0.7%.

In some embodiments, pharmaceutical compositions for use in the methods of this invention comprise solutions or emulsions, which in some embodiments are aqueous solutions or emulsions comprising a safe and effective amount of the composition of the present invention and optionally, other compounds. In some embodiments, the compositions comprise from about 0.01% to about 10.0% w/v or w/w of a combination of active ingredients as described herein.

Further, in another embodiment, the compositions are administered topically to body surfaces, and are thus formulated in a form suitable for topical administration. Suitable topical formulations include gels, ointments, creams, lotions, drops and the like. For topical administration, the composition of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, compositions include aqueous solutions of the active preparation in water-soluble form. Additionally, suspensions of the active ingredients, in some embodiments, are prepared as appropriate oily or water based suspensions. Suitable lipophilic solvents or vehicles include, in some embodiments, fatty oils such as sesame oil, or synthetic fatty acid esters such as ethyl oleate, triglycerides or liposomes. Aqueous suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In some embodiments, compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as nutraceutical or pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a nutraceutical or a pharmaceutically-acceptable carrier to be used in conjunction with the compound is basically determined by the way the compound is to be administered. If the subject compound is to be injected, in one embodiment, the nutraceutical or pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material, the compositions of the invention, into or onto particulate preparations of polymeric compounds such as polylactic acid, polglycolic acid, hydrogels, etc, or onto liposomes, microemulsions, micelles, unilamellar or multi-lamellar vesicles, erythrocyte ghosts, or spheroplasts.) Such compositions will influence the physical state, solubility, stability, rate of in vivo release, and rate of in vivo clearance. Also comprehended by the invention are particulate compositions coated with polymers (e.g. poloxamers or poloxamines).

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the composition described herein can be determined by standard nutraceutical or pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical or nutraceutical carrier are also be prepared, placed in an appropriate container, and labeled for treatment of an indicated condition.

In one embodiment, compositions of the present invention are presented in a pack or dispenser device, such as an FDA approved kit, which contain one or more unit dosage forms containing the composition. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of nutraceuticals or pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include chemical, molecular, biochemical, and cell biology techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); "Cell Biology: A Laboratory Handbook", Volumes I-III Cellis, J. E., ed. (1994); The Organic Chemistry of Biological Pathways by John McMurry and Tadhg Begley (Roberts and Company, 2005); Organic Chemistry of Enzyme-Catalyzed Reactions by Richard Silverman (Academic Press, 2002); Organic Chemistry (6th Edition) by Leroy "Skip" G Wade; Organic Chemistry by T. W. Graham Solomons and, Craig Fryhle.

Material and Methods

Cells

Macrophage isolation and culture Peritoneal macrophages were collected from the peritoneal cavity of 6- to 8-week-old male ICR mice (Harlan, Israel) after an intraperitoneal injection of 1.5 ml of thioglycollatebroth (4%) 4 days before harvest. Peritoneal macrophages were washed three times with phosphate-buffered saline (PBS) and, when appropriate, a hypotonic lysis of erythrocytes was performed, yielding a highly enriched (90-95%) macrophage cell population. Macrophages were identified by FACS (Becton-Dickinson, Mountain View, Calif., USA) analysis using FITC-conjugated rat anti-mouse F4/80 (MCA497F; Serotec, Oxford, UK) by flow microfluorimetry. For each sample, 10,000 light-scatter-gated viable cells were analyzed. Peritoneal macrophages ($1\times10^6$ cells/well) were cultured in 96-well-plates at 37° C. in a 5% $CO_2$ atmosphere in RPMI 1640 medium containing 10% fetal calf serum, 2 mM L-glutamine. 100 U/ml penicillin. 100 mg/ml streptomycin (Beit-Haemek, Israel). Cells were stimulated with 1 mg/ml LPS from *Salmonella enterica* serotype *typhimurium* in the absence or presence of different combination as described herein (see the figures in the examples section). The phytonutrients were dissolved in dimethylsulfoxide (DMSO; in a final concentration of 5 mM). The mixture was vortexed and incubated in a water bath at 37° C. (with shaking) for 10 mins and sonicated in a sonicator bath for 15 seconds three times. Working concentrations of the compounds were prepared from the stock solution by addition of appropriate volumes to warmed culture medium. The final concentration in solution was calculated by addition of 0.5 ml isopropanol and 1.5 ml hexane/dichloromethane (1/5 v/v) containing 0.025% BHT to 1 ml of the culture medium. The solution was vortexed and the liquid phases were separated by centrifugation at 3000 rpm for 10 min. Spectrophotometry was performed to measure the concentrations of lycopene, asthaxanthin, lutein, b-carotene. To the controls appropriate volumes of DMSO (0.1-0.2%) were added and the percentage inhibition in each tube test was calculated in relation to its control.

TNF-Alpha Production Assay

Concentrations of TNF-alpha in cell culture supernatants were quantified by ELISA kits (Biolegend, SanDiego, Calif., USA).

Example 1

The Anti-Inflammatory Effect of the Composition of the Present Invention on Macrophages The anti-inflammatory effect was detected by inhibition of NO production and of TNF alpha production by LPS-stimulated macrophages.

The figures below show that astaxanthin inhibited NO (FIG. 1) and TNF alpha production (FIG. 3) in a dose dependent manner.

This experiment proved the synergetic inhibition (p<0.001 compared with the additive effect) by combinations of astaxanthin in the range of 0.5-2 μM with 1 μM Tomato Lycopene extract LycoMato (LM), but not with 1 μM lutein or 1 μM carnosic acid (FIGS. 1 and 3). The letter S above the horizontal lines determine the synergistic effect Addition of 1 μM carnosic acid to the combinations of astaxanthin in the range of 0.1-1 μM with 1 μM LycoMato (LM) caused a synergetic inhibition (p<0.001 compared with the additive effect) (FIGS. 2 and 4) that was higher than the effect achieved in the absence of carnosic acid.

The inhibitory effect of the combinations of astaxanthin with LycoMato and lutein was lower than that of astaxanthin with LycoMato and carnosic acid (FIGS. 2 and 4).

Finally, the effect of the four phyto-nutrients was not significantly different from the effect of asthaxanthin with LycoMato and carnosic acid (FIGS. 2 and 4).

Example 2: Tomato Lycopene is Far More Effective than Synthetic Lycopene in its Anti-Inflammation Activity as Measured by NO Production Tomato lycopene extract was found to be far more effective than synthesis lycopene in reducing NO production by macrophages (FIG. 5). Synergistic inhibition for the secretion of proinflammatory mediators by LPS-stimulated macrophages pre-incubated with combinations of Lyc-O-Mato® with lutein, astaxanthin, b-carotene, and carnosic acid, was recorded. This novel combination was found to be unexpectedly efficacious for the current medical indications.

Moreover, a synergistic inhibition for the production of NO by LPS-stimulated macrophages pre-incubated with a combination of Lyc-O-Mato® (LM) and astaxanthin was recorded (FIG. 1).

As shown in FIG. 2 a synergistic inhibition for the production of NO by LPS-stimulated macrophages pre-incubated with a combination of: (1) Lyc-O-Mato® (LM), carnosic acid, and astaxanthin or (2) Lyc-O-Mato® (LM), lutein, and astaxanthin, were recorded.

As shown in FIG. 3 a synergistic inhibition for the production of TNF-alpha by LPS-stimulated macrophages pre-incubated with a combination of Lyc-O-Mato® (LM) and astaxanthin was recorded.

As shown in FIG. 3 a synergistic inhibition for the production of TNF-alpha by LPS-stimulated macrophages pre-incubated with a combination of: (1) Lyc-O-Mato® (LM), carnosic acid, and astaxanthin, (2) Lyc-O-Mato® (LM), lutein, and astaxanthin, or (3) Lyc-O-Mato® (LM), carnosic acid, lutein and astaxanthin, were recorded.

Example 3: The In-Vivo Anti-Inflammatory Effect of a Mixture Tomato Lycopene Extract+Astaxanthin+Carnosic Acid was Determine in a Mouse Model of Sterile Peritonitis Methods
Mouse Model of Sterile Peritonitis—
Six to eight weeks old male ICR mice (Harlan Laboratories, Israel), average weight 30 gr, were fed ad libitum rodent chow (#19520 Kofolk, Pethach Tikva, Israel) and free reverse osmosis filtered water. Animals were housed in static microisolator cages with sterile pine shaving bedding in 12:12 light dark cycles 18-26 Celsius degrees and 30-70% relative humidity. Mice received in their drinking water a supplementation of Lyc-O-Mato®, Astaxanthin, Carnosic acid at the ratio of 1:0.5:1 (The quantity of Lyc-O-Mato® used was 10 mg/kg) during 7 days before induction of peritonitis. This supplementation was prepared in microemulsion containing: 0.3% ascorbyl palmitate, 0.3% alpha tocopherol, 9.34% medium chain triglycerides 13% polysorbat 80. The micro-emulsion without any nutrients served as placebo. The animals drank 4 ml/water per day; thus the phytonutrient intake of Lyc-O-Mato®, lutein, carnosic acid was 10:4.9:6.6 mg/Kg/day, respectively. Sterile peritonitis was induced by intraperitoneal injection of a sterile thioglycollate solution (4% w/v in PBS). In this model neutrophils are recruited to the peritoneal cavity (the site of inflammation) during the first 24 h and than replaced by monocyte-macrophages. Peritoneal cells were harvested after 24 h to isolate neutrophils or after 4 days to collect macrophages using two washes of the peritoneal cavity with 8 ml RPMI medium. Peritoneal cells were washed three times with PBS and, when appropriate, hypotonic lysis of erythrocytes was performed, yielding a high homogenous (90%) neutrophil cell population harvested 24 h after the induction of peritonitis and a high homogenous (90%) macrophage cell population collected 4 days later. Peritoneal cells were identified by flow microfluorimetry on FACS (Becton Dickinson, Mountain View, Calif.) using FITC-conjugated rat anti-mouse neutrophils (MCA771F), FITC-conjugated rat anti-mouse F4/80 (MCA497F), and FITC-conjugated rat anti-mouse CD3 (MCA500F) (Serotec, Oxford, England) for the characterization of neutrophils, monocyte-macrophages and lymphocytes, respectively.

Body Weight
The body weights of each mouse was taken on the first day of the nutrient or placebo supply and at termination. There was no difference in weight gain between the groups studied.

Superoxides Production by Neutrophils
The production of superoxide anion ($O_2^-$) by neutrophils was measured as the superoxide dismutase-inhibitable reduction of ferricytochrome c by the microtiter plate technique. Neutrophils ($5 \times 10^5$ cells/well) suspended in 100 μl HBSS containing ferricytochrome c (150 mM). Stimulation was induced with PMA (50 ng/ml). The reduction of ferricytochrome c was followed by a change of absorbance at 550 nm at 2 min intervals for 30 min on a Thermomax Microplate Reader (Molecular Devices, Melno Park, Calif., USA). The maximal rates of superoxide generation were determined and expressed as nanomoles $O_2^-/10^6$ cells/10 min using the extinction coefficient $E_{550} = 21$ mM$^{-1}$ cm$^{-1}$.

Macrophage Cell Culture
Peritoneal macrophages were cultured in RPMI 1640 medium containing 10% FCS, 2 mM L-glutamine, 100 U/ml penicillin, 100 μg/ml streptomycin (Beit-Haemek, Israel) in 96-well plates ($2 \times 10^5$ cells/well). LPS was added and the macrophages were cultured at 37° C. in 5% $CO_2$ atmosphere for 16-24 h.

NO Production Assay
NO levels in supernatants of cell cultures were determined by assaying nitrite levels using Griess reagent and sodium nitrite as a standard.

$PGE_2$ Production Assay
Supernatants of cell cultures were collected and immediately stored at −70° C. $PGE_2$ levels were determined by utilizing dextran coated charcoal radioimmunoassay protocol. Briefly, 100 μl sample or $PGE_2$ standard (Sigma Israel, Rehovot, Israel) were incubated in the presence of 500 μl anti-$PGE_2$ anti-serum (Sigma Israel, Rehovot, Israel) for 30 min. [³H]PGE$_2$ (Amersham Biosciences, NJ, USA) was added next for 24 h at 4° C. 24 h later, 200 µl cold dextran coated charcoal suspension was added to each tube and incubated for 10 min on ice. The tubes were centrifuged at 3500 RPM for 15 min at 4° C. 500 µl of supernatants containing [³H]PGE$_2$-anti-PGE$_2$ complexes were counted (Packard Spectrometry 1900CA) and the amount of PGE$_2$ was calculated.

TNFα Production Assay

Concentrations of TNFα in supernatants of cell cultures, that were collected and immediately stored at −70° C., were quantified by ELISA kits (Biolegend Inc., San Diego, Calif.).

Statistical Analysis

Data are presented as the mean±SEM. Statistical significance for comparisons between groups was determined using Student's paired two-tailed t-test.

Results

Figure 6A:
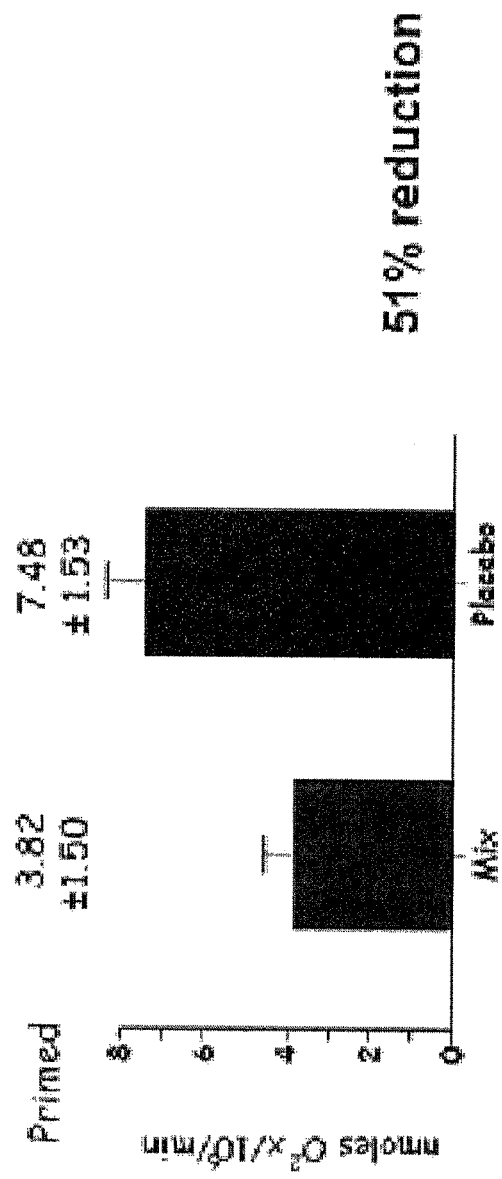
FIGS. 6A-6B are bar graphs representing superoxide production by non stimulated peritoneal cells. The cells were activated (FIG. 6B) or primed (FIG. 6A) due to the thioglicollate peritoneal injection and reflect the situation of the cells in a site of inflammation. As shown there is a significant ($p<0.01$) reduction (39%) in the release of superoxide by the nutrient mixture treatment compared with the placebo (3.82+1.52 compared with 6.22±1.53 nmoles $O_2/10^6$ cells/min, respectively).
Figure 6B:
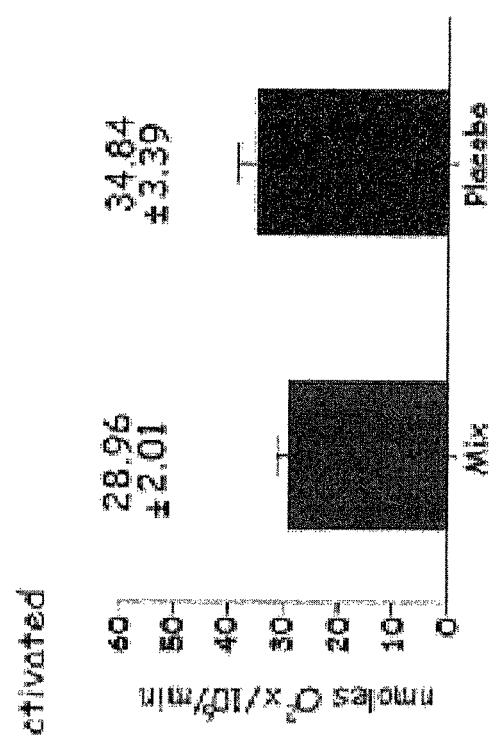

Superoxide production was measured in mice peritoneal neutrophils isolated at 24 h of peritonitis induction (n=10 mice in each group). FIG. 6 presents superoxide production by non stimulated peritoneal cells. These cells are primed due to the thioglicollate peritoneal injection and reflect the situation of the cells in a site of inflammation. As shown there is a significant ($p<0.01$) reduction (39%) in the release of superoxide by the nutrient mixture treatment compared with the placebo (3.82±1.52 compared with 6.22±1.53 nmoles O$_2$/10$^6$ cells/min, respectively).

Moreover, stimulation of the cells (as in case of infections) resulted with an effective release of superoxides (7.5 fold higher than without stimulation) and with no significant differences (p=n.s.) in superoxide release by cells of placebo mice (28.96 and 34.84 nmoles O$_2$/10$^6$ cells/min, respectively). The rate of stimulates superoxide production of cells from the supplementation (mix) treated mice is sufficient to combat infection.

These results demonstrate the significant anti inflammatory effect of the combination of LycoMato, Astaxanthin and Carnosic acid mixture that significantly reduced the release of spontaneous free radicals by neutrophils arriving to the site of inflammation. Thus the nutrient feeding prevented the delirious effect of neutrophils in the site of inflammation but did not diminish their potential to release superoxide when attacked by infection.

The anti-inflammatory effect of the nutrient treatment was studied also on pro-inflammatory agents released by macrophages at the site of inflammation. Mice received the supplementation or placebo for 7 days before induction of peritonitis for 4 days (n=10 mice for each group). Supernatant of isolated peritoneal cells cultured for 24 h with 0.5 ug/ml LPS was analyzed for NO production, PGE$_2$ production and TNFα production.

Figure 7A:
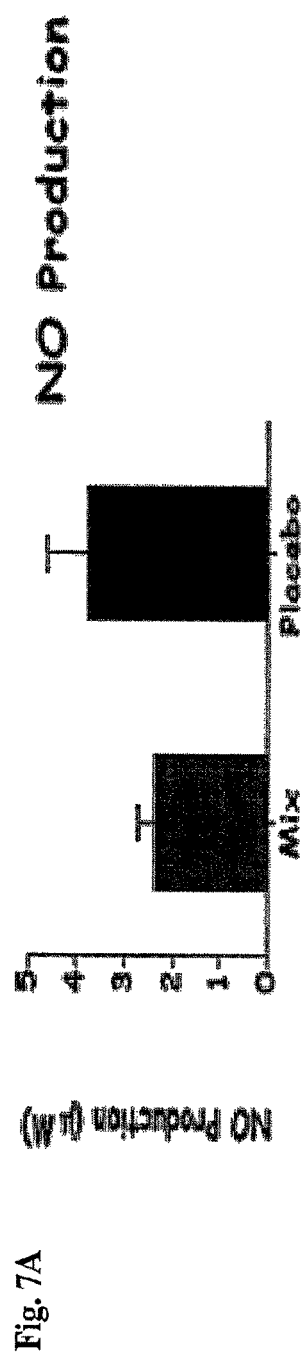
FIGS. 7A-7C are bar graphs showing the reduction (significance $p<0.05$) in NO production (FIG. 7A) by peritoneal cells harvested from mice undergoing nutrient drinking compared with placebo; 2.35+0.36 compared with 3.72+0.88 µM, respectively. Similarly, there is a reduction (significant $p<0.05$) in $PGE_2$ production (FIG. 7B) and TNF alpha production (FIG. 7C) by peritoneal cells harvested from mice undergoing the nutrient drink of the invention compared with placebo, 1.75+0.26 compared with 2.72+0.33 ng/ml.
Figure 7B:
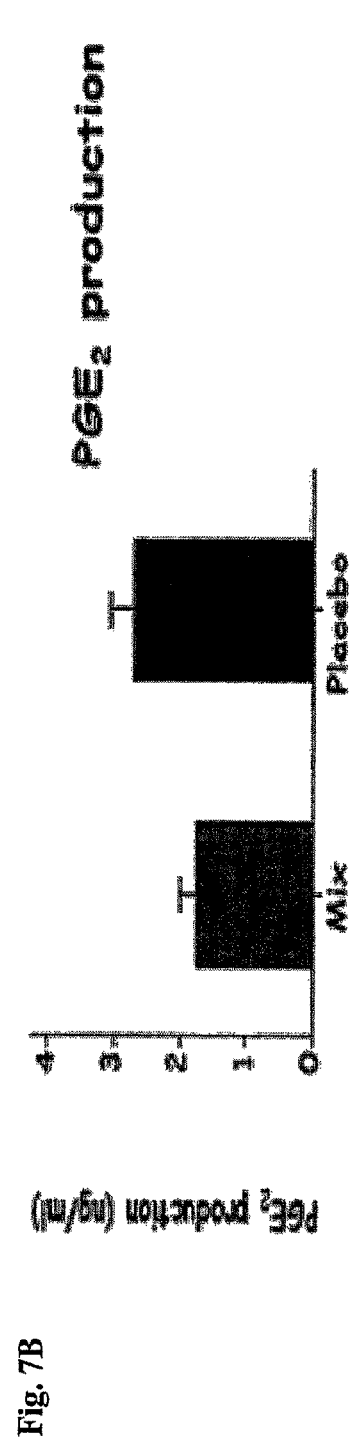
Figure 7C:
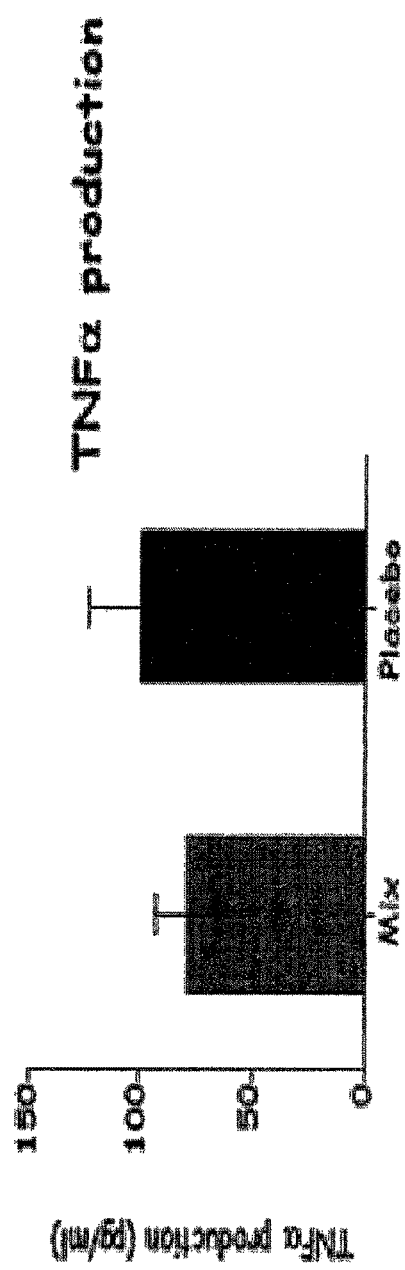

As shown in FIG. 7, there is a reduction (significance $p<0.05$) in NO production by peritoneal cells harvested from mice undergoing nutrient drinking compared with placebo; 2.35±0.36 compared with 3.72±0.88 µM, respectively. Similarly, there is a reduction (significant $p<0.05$) in PGE$_2$ production by peritoneal cells harvested from mice undergoing nutrient drinking compared with placebo, 1.75±0.26 compared with 2.72±0.33 ng/ml. Like wise TNFα production by peritoneal cells harvested from mice undergoing nutrient drinking compared with placebo, 78.91±13.8 compared with 99.55±24.03 pg/ml.

The invention claimed is:

1. A composition comprising astaxanthin and tomato lycopene, wherein the molar concentration ratio of astaxanthin to tomato lycopene is from 1:2 to 2:1.

2. The composition of claim 1, wherein said composition is an oral composition.

3. The composition of claim 1, further comprising a nutraceutical or a pharmaceutical acceptable excipient.

4. The composition of claim 1, wherein said composition has a synergistic anti-inflammatory effect.

5. A method of treating a subject afflicted with inflammation, comprising the step of administering to said subject a therapeutically effective amount of a composition comprising astaxanthin, and tomato lycopene in a molar concentration ratio of said astaxanthin to said tomato lycopene from 1:2 to 2:1, thereby treating a subject afflicted with inflammation.

6. The method of claim 5, wherein said treating a subject afflicted with inflammation is inhibiting the production of a pro-inflammatory mediator in a macrophage at a site of inflammation in said subject.

7. The method of claim 5, wherein said treating a subject afflicted with inflammation is inhibiting the production of NO, PGE2, TNF-alpha, or any combination thereof in said subject.

8. The method of claim 5, wherein said treating a subject afflicted with inflammation is inhibiting the recruitment of neutrophils to the site of inflammation, inhibiting neutrophils activation at the site of inflammation, or a combination thereof in said subject.

9. The method of claim 5, wherein the composition is an oral composition.

10. The method of claim 5, wherein the composition further comprises a nutraceutical or a pharmaceutical acceptable excipient.

* * * * *